United States Patent [19]

McEachern et al.

[11] 4,094,310
[45] June 13, 1978

[54] APPARATUS FOR ENHANCED DISPLAY OF PHYSIOLOGICAL WAVEFORMS AND FOR DEFIBRILLATION

[75] Inventors: Robert A. McEachern, Wellesly; George A. Cavigelli, Lexington, both of Mass.

[73] Assignee: American Optical Corporation, Southbridge, Mass.

[21] Appl. No.: 729,442

[22] Filed: Oct. 4, 1976

[51] Int. Cl.² .............................................. A61B 5/04
[52] U.S. Cl. ......................... 128/2.06 G; 128/419 D; 315/384; 346/33 ME
[58] Field of Search ..................... 128/2.06 A, 2.06 G, 128/2.06 R, 2.05 R, 419 D, 419 PT; 340/33 ME; 315/377, 383, 384, 30

[56] References Cited

U.S. PATENT DOCUMENTS

| 3,267,933 | 8/1966 | Mills et al. | 128/2.06 A |
|---|---|---|---|
| 3,442,269 | 5/1969 | Druz | 128/419 D |
| 3,562,557 | 2/1971 | Gates | 315/384 |
| 3,626,932 | 12/1971 | Becker | 128/2.06 R |
| 3,672,353 | 6/1972 | Crovella et al. | 128/2.06 A |
| 3,835,845 | 9/1974 | Maher | 128/2.06 R |
| 3,874,370 | 4/1975 | Harris et al. | 128/2.06 G X |
| 3,897,774 | 8/1975 | Burdick et al. | 128/419 PT |

*Primary Examiner*—William E. Kamm
*Attorney, Agent, or Firm*—Jeremiah J. Duggan; Stephen A. Schneeberger

[57] ABSTRACT

A system for the enhanced display of event markers in time-related association with physiological waveforms displayed on cathode ray tubes which use a recirculating memory to provide a refreshed display. The event is marked in the displayed waveform by an intensification of the normal trace determined by the time-related occurrence of the event and comprises a first modulation of the displayed waveform. A secondary event-controlled modulation of the primary modulated display serves to further enhance and accurately identify the occurrence and timing of the event marker in the display. This enhanced display of event markers is further utilized to distinguish a marker of one type from a marker of another type utilizing particular data coding in the memory and appropriate detection logic for recovering data from memory. The enhanced display is particularly useful for clearly marking events occurring in timed-relationship with a patient's cardiac cycle.

19 Claims, 7 Drawing Figures

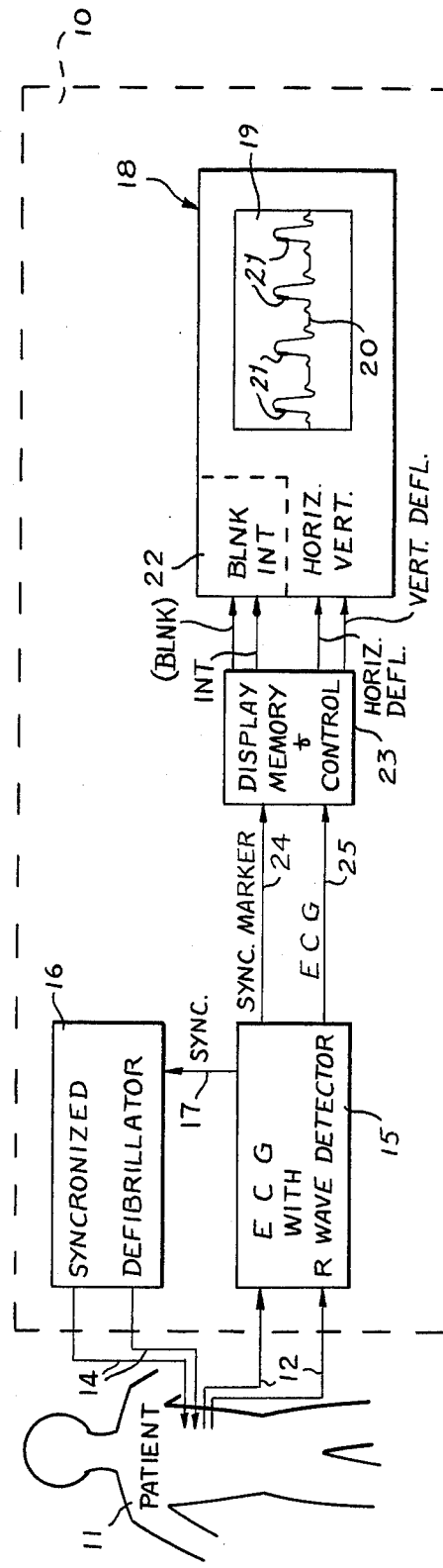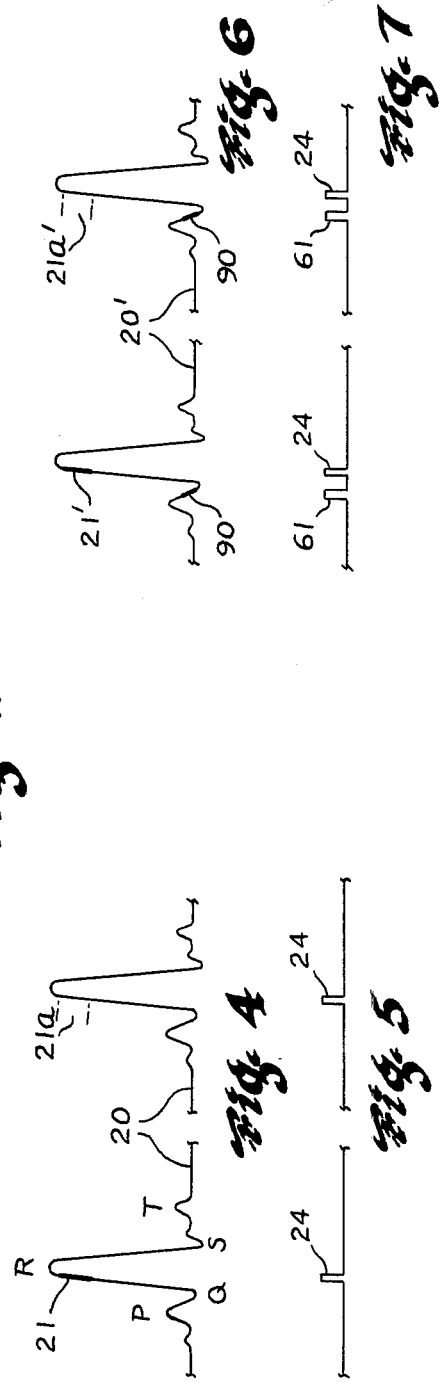

APPARATUS FOR ENHANCED DISPLAY OF PHYSIOLOGICAL WAVEFORMS AND FOR DEFIBRILLATION

BACKGROUND OF THE INVENTION

The present invention relates generally to visual display systems. More particularly, the present invention relates to visual displays for physiological waveforms. Even more particularly the present invention relates to enhanced displays for physiological waveforms.

Visual display systems using cathode ray tubes are well known in the electronics art. Additionally, cathode ray tube (CRT) display systems are known for the visual display of various vital sign signals of patients, and particularly for the display of physiological waveforms. In such displays of physiological waveforms it may be desirable to indicate or mark the occurrence of some event relative to the displayed waveform. For instance, in cardioresuscitation systems having a defibrillator capable of operation in a synchronized mode and an accompanying CRT for display of a patient's ECG waveform, it may be desirable to visually indicate to the operator exactly when in the cardiac cycle the discharge of defibrillating energy will occur. Such visual evidence of the sync pulse which times the defibrillator's discharge is reassuring to the operator and permits verification of the correctness of its timing in the cardiac cycle, particularly as related to the so-called vulnerable period of the cycle.

Because of the importance of such event markers which are of usually short duration in the cardiac cycle, it is important that they be highly visible and distinctly displayed on the CRT monitor. Although deflection of the CRT's electron beam, either vertically or horizontally, from the normal trace of the displayed physiological waveform is one possible means of visually marking the occurrence of the particular event relative to the waveform, a marker provided by such technique may be limited in intensity and clarity due to writing speed limitations caused by slew-rate limitations of the circuitry and/or speed limitations of the CRT's phosphor. This problem is particularly evident in "refreshed" or "non-fade" displays in which the data to be displayed is recirculated at a fast rate within a recirculating memory. Such displays may either be stationary or may precess and permit one or more full cardiac cycles of the ECG waveform to continuously appear on the CRT, thereby facilitating the observer's correlation of the event marker with the remainder of the cardiac cycle. In either event, the sweep frequencies of the CRT beam are sufficiently high and the normal circuitry associated therewith sufficiently slew-rate limited that it becomes difficult to rapidly deflect the electron beam from the trace of the waveform with sufficient amplitude to comprise the marker and yet also with the speed needed to prevent significant distortion to the basic waveform. Further, the relatively high writing speed required of such a marker deflection inherently results in a diminished display intensity.

Distortion of the basic waveform may be particularly noticeable in those situations in which the marker occurs on the relatively steep slope of certain types of physiological waveforms, as for instance the R-wave of the cardiac cycle.

Although many of these problems are overcome by changing (increasing) the intensity of the electron beam each time the event marker occurs in the sweep, there may be random increase in intensity at other portions of the waveform trace which prove confusing. For instance, the base line and other portions of the waveform which do not vary rapidly in the vertical direction may normally appear brighter than portions which vary rapidly in the vertical direction.

The aforementioned problems regarding certain types of event markers may be further complicated if markers for different types of events are to be included and must be separately recognizable on the display.

Accordingly, it is a principal object of the invention to provide a system for enhancing the display of physiological waveforms. Included within this object is the provision of means for clearly distinctly, and unambiguously marking events on the displayed physiological waveform.

It is a further object of the invention to provide enhanced display of event markers on physiological waveforms visually displayed by non-fade or refreshed displays employing a cathode ray tube. Included in this object is the provision of an event marker which minimizes distortion of the basic physiological waveform. Still further included within this object is the provision of a clear and distinct event marker occurring during an interval of steep slope in the displayed physiological waveform.

It is a still further object of the present invention to provided enhanced and non-ambiguous display of the event markers associated with different types of events associated with a particular physiological waveform.

SUMMARY OF THE INVENTION

The present invention relates to the enhanced display of event markers associated with the cathode ray tube display of physiological waveforms by employing intensity modulation of the electron beam. Display control circuitry is provided for controlling the deflection of the CRT beam in at least one, and normally two, coordinate directions and for controlling the intensity of the beam. Circuitry exists for generating an electrical signal representative of the particular physiological waveform being displayed, which signal is applied to the display control circuitry for controlling the deflection of the CRT beam in the at least one coordinate direction. Further circuit means generate an electrical signal indicative of the occurrence of a preselected event in timed relation to the physiological waveform signal. The event signal generating circuitry is normally responsive to the physiological waveform for recognizing the preselected event. The display control circuitry of the CRT includes a recirculating memory and circuitry for varying the intensity of the beam trace as a first or primary function of the preselected event signal and for secondarily varying or modulating the primarily modulated beam trace during the interval of the event signal. Inasmuch as it is desired to highlight the occurrence and timing of the preselected event relative to the displayed physiological waveform, the event signal preferably acts to increase the intensity of the beam and accordingly the trace displayed on the face of the CRT as the primary mode of modulation, and periodically blanks the intensification of the first mode to comprise the secondary mode of modulation. The secondary mode of modulation may alternatively comprise a variation in the duration or magnitude of the primary modulation.

The present invention is particularly suited to non-fade or refreshed displays in which the data for display is stored in a recirculating memory, which memory may additionally provide for the precession of the displayed waveform across the face of the CRT in a manner known in the prior art. In a preferred embodiment, the physiological waveform signal is converted to digital samples stored in a digital, recirculating memory for providing a precessing display. Similarly, the signal representative of the preselected event is entered, in digital form, in the same recirculating memory in the appropriately timed relationship with the physiological waveform data samples and is recirculated in synchronization therewith.

In one embodiment of the invention, the memory is comprised of plural parallel data tracks, with the physiological waveform data being stored and recirculated in some, but not all, of the data tracks and the event data being stored and recirculated in at least one other different one of the parallel data tracks. Detection circuitry is separately associated with those data tracks carrying the physiological waveform data and that (or those) track carrying the event data such that the two are separately read out of memory in parallel. The waveform data may then be converted to an analog signal for controlling the vertical (magnitude) deflection of the CRT beam. The detected event data controls the primary modulation of the intensity of the CRT beam and, in combination with a periodic control signal, controls the secondary modulation of the beam.

In another embodiment of the invention in which there occur events of different type and for which recognizably different event markers are to be provided on the trace of the physiological waveform, the memory is divided into a number of serially recirculated, multibit words. The coding of the data entered in the respective word positions in memory is controlled such that each waveform-sample word is recognizably different from any event-word and further, event words associated with one type of event are recognizably different from event words associated with another type of event. The detection circuitry for reading data out of memory includes a logic responsive to the different codings of the words stored in memory for respectively identifying and distinguishing for readout the waveform data, and each different type of event data. Although each type of event marker data may serve to increase the intensity of the CRT beam tracing the physiological waveform for the primary modulation, further circuitry responsive to the difference in the differing event marker data serves to further distinguish an event marker of one type from an event marker of another type by secondarily modulating the intensity of at least one but less than all of the different types of event markers.

In a particular embodiment of the invention, the physiological waveform displaying system operates in conjunction with a cardioresuscitation system having a synchronized defibrillator and electrocardiographic (ECG) signal developement circuitry such that a patient's cardiac cycle of ECG waveform comprises the physiological waveform being displayed and the event marker of interest represents the relatively-timed recognition of an R-wave in the ECG signal and the resultant generation of a sync pulse for controlling the synchronized discharge of defibrillating energy to the patient. In yet another embodiment, circuitry of a known type is provided for recognizing a heart pacer stimulation pulse appearing in the patient's ECG and accordingly, serves to provide a second event marker signal in addition to the defibrillator sync marker, the markers displayed for the two different events each being an intensification of the normal waveform trace, but with a preselected one of the two markers flashing on and off at a visibly perceptable rate.

BRIEF DESCRIPTION OF THE DRAWINGS

FIG. 1 is a block diagram of an illustrative system embodying the display system of the invention;

FIG. 4 depicts an electrocardiographic waveform in which a defibrillator sync pulse marker is provided by an intermittant intensification of the trace in the upslope of the R-wave;

FIG. 5 is a waveform illustrating the sync marker signal and its timing relative to the ECG waveform in FIG. 4;

FIG. 6 is an ECG waveform similar to that of FIG. 4 and showing constant intensification at one place and intermittant intensification at another in the cardiac cycle to represent two different event markers;

FIG. 7 is a waveform depicting the timing of a pacer stimulation pulse marker signal and a defibrillator sync marker signal relative to the ECG waveform of FIG. 6.

DESCRIPTION OF THE PREFERRED EMBODIMENTS

Figure 2:
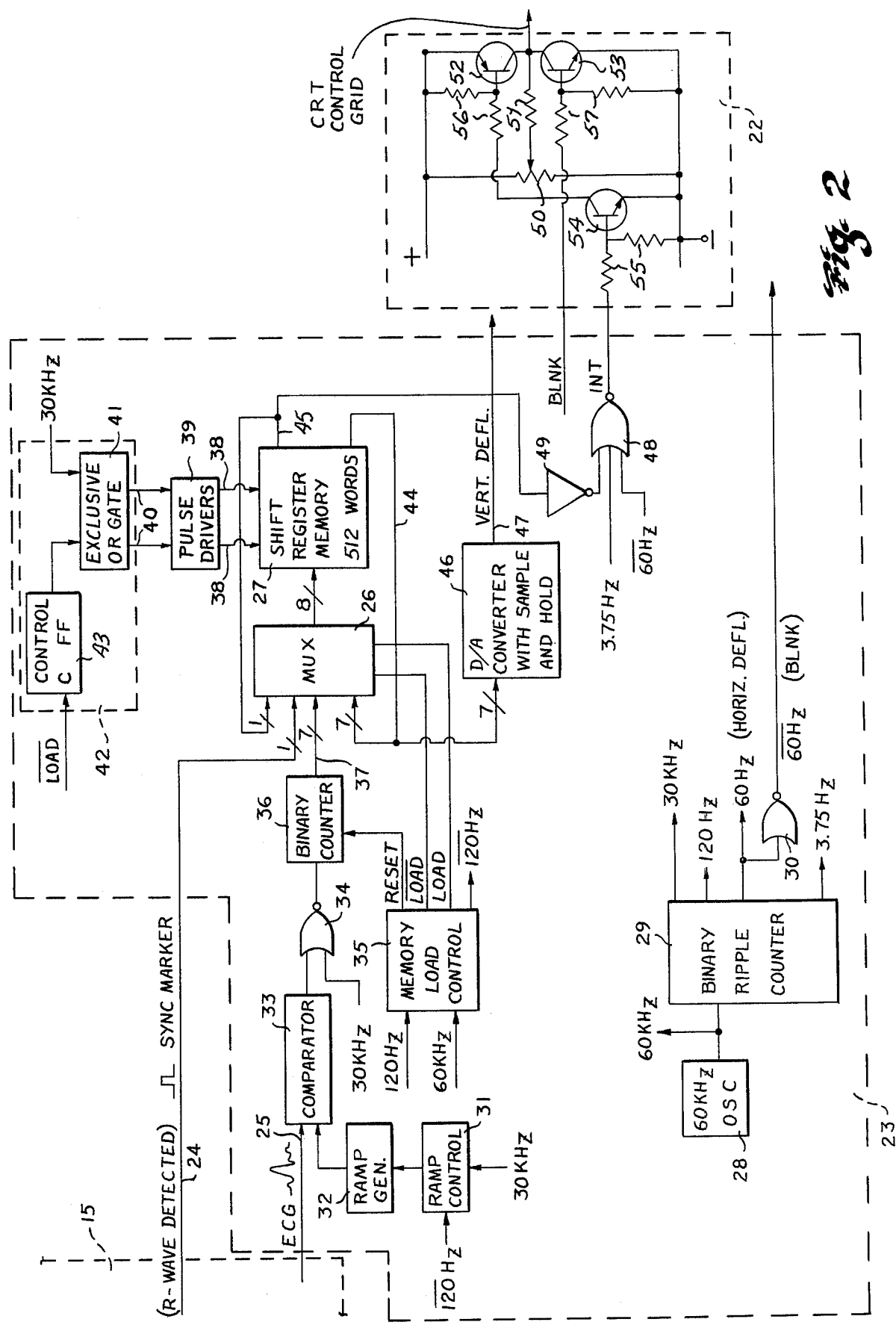
FIG. 2 is a block diagram of certain portions of the illustrative system of FIG. 1 showing the display system of the invention in greater detail.

FIG. 1 depicts a cardioresuscitation system 10 operatively connected to a patient 11 via electrode cable pair 12 and electrode cable pair 14. Electrodes (not shown) associated with cable pair 12 sense the electrical activity associated with the beating of the heart of patient 11 and extend the electrical signal, as an ECG signal, to ECG signal amplifying circuitry 15 which includes circuitry of a known type for detecting the occurrence of the R-wave in the normal PQRST complex associated with an ECG waveform. Such R-wave detection circuitry normally responds to signal magnitude and/or slope and/or frequency such that the R-wave in a normal mophology is recognized part-way up its steeply rising leading edge. The cardioresuscitation system 10 includes a defibrillator 16 capable of operation in a synchronized mode, as described in the U.S. Pat. No. 3,236,239 of February 22, 1966 to Berkovits for DEFIBRILLATOR. The synchronized defibrillator 16 provides a discharge of electrical energy to patient 11 via cables 14 to cause a fibrillating heart to revert to its normal rhythm. As described in the aforementioned U.S. Pat. No. 3,236,239, it has been recognized that discharge of defibrillating energy to a patient during certain so-called "vulnerable" portions of the cardiac cycle (generally coinciding with the T-wave portion of the PQRST complex) may be fatal to the patient. In order to prevent the operation from discharging the defibrillation energy to the patient at some random time in the cardiac cycle, means were provided in the above referenced patent for monitoring the patient's ECG waveform and detecing when the R-wave portion thereof occurred, such detection of the R-wave then serving to generate a synchronization, or sync pulse represented by line 17 which is then extended to gating circuitry associated with defibrillator 16 to allow selective discharge of defibrillating energy to the patient 11 by the operator only during the existence of the sync pulse.

A visual display unit 18 including cathode ray tube 19 is provided with the cardioresuscitation system 10 to allow a doctor or other operator to monitor the displayed waveform 20 corresponding with the ECG of patient 11. It is reassuring to the operator to have the existence and relative timing of the sync pulse on line 17 displayed in successive cardiac cycles in order to confirm its accuracy or otherwise to take alternative safe action. Accordingly, a marker 21 appears in the display waveform 20 each time a sync pulse is extended on line 17 to defibrillator 16, this normally occurring once during each cardiac cycle. According to the invention, event markers 21 appear in the displayed waveform 20 (seen more clearly in FIG. 4) and are provided by primarily modulating the intensity of the electron beam which forms the visible trace on the face of CRT 19 during occurrence of an event and also secondarily modulating the first mode of modulation. More specifically, in the illustrated embodiment, the event markers 21 are represented by periodic increases in the intensity of brightness of waveform 20 at the time of occurrence of the event being marked.

The display unit 18 includes a blanking and intensity control circuit 22 by which the intensity of the electron beam, and thus its resultant trace, is regulated. Further, display unit 18 includes conventional means for controlling the horizontal and vertical deflection of the CRT beam in response to input control signals thereto. Inasmuch as display unit 18 is of the non-fade type, the horizontal beam will be repeatedly swept in a trace mode at a high repetition rate (i.e. 60 Hz), with the blanking circuitry 22 being operative to suppress the electron beam and thereby blank the trace during the retrace portion of each horizontal sweep cycle. A control signal (in analog form in the present embodiment) representing the ECG waveform is applied to the input of the vertical deflection circuitry such that the electron beam, and accordingly the displayed trace, is deflected vertically in accordance with the magnitude vs time function of the ECG signal. The intensity control input (INT) to blanking and intensity control circuit 22 is provided by a control signal which is normally in one state during most of the trace mode of each sweep cycle such that the trace of waveform 20 is of "normal" or moderate intensity, and may be in another state during the other time in the trace portion of each cycle in which the SYNC signal on line 17 exists to temporarily increase the intensity of the trace of waveform 20.

A display memory and associated control circuitry 23 respond to a SYNC MARKER signal, represented by line 24, and the analog ECG signal, represented by line 25, from the ECG amplifier 15 for storing and recirculating samples of the SYNC MARKER and the ECG signals to provide a non-fade or refreshed display on the face of CRT 19. The memory and control circuitry 23, though illustrated apart from display unit 18 in FIG. 1, comprises an integral portion of the display system comprising the invention and might alternatively have been shown as part of display unit 18.

SYNC MARKER signal represented by line 24 bears a fixed time-relationship to the SYNC signal represented by line 17, and in the interest of simplicity will, in the present embodiment, be considered as being coincident therewith. It will be appreciated, however, that the SYNC MARKER signal might coincide substantially with the detection of the R-wave by R-wave detector 15, whereas the actual SYNC pulse represented by line 17 might be delayed by some short interval (e.g. 20 milliseconds) as described in the aforementioned U.S. Pat. No. 3,236,239. The timing and duration of the SYNC MARKER pulse relative to the ECG waveform 20 of FIG. 4 is represented by the waveform of FIG. 5.

For a more complete understanding of one embodiment of the invention, and particularly the display memory and control circuitry 23 and the blanking and intensity control circuitry 22 thereof, reference is made now to FIG. 2. The memory is a multiplexed dynamic shift register comprised of a multiplexer 26 and a shift register 27 comprised of four, dual 512-bit chips with on-chip multiplexing. Shift register 27 accordingly constitutes a memory of 512 eight-bit words with 7 bits of each word being devoted to ECG data and the remaining bit being devoted to SYNC MARKER data. The memory of the illustrated embodiment is of the digital type, though an analog memory might alternatively be employed if digital processing is not preferred.

The basic timing for the shift register memory 27 and the various other control circuits for display unit 18 is provided by a 60 kHz oscillator 28 driving a binary ripple counter 29 to supply, in addition to the 60 kHz timing signal, a 30 kHz timing signal, a 120 Hz timing signal, a 60 Hz timing signal which additionally, following inversion by inverter 30, provides a 60 Hz timing signal, and a 3.75 Hz flasher signal in accordance with the invention. The 30 kHz signal is a source of shift pulses for the shift register memory 27 and also comprises an input to the analog-to-digital converter which converts the analog ECG signal on line 25 to digitized samples. The 120 Hz signal provides the source or control for the 120 samples-persecond (one sample every 8.3 milliseconds) sampling rate at which the ECG signal on line 25 is digitalized. The 60 Hz timing signal (HORIZDEFL) is extended to the input of the horizontal deflection circuitry (HORIZ) of display equipment 18 such that it generates a triangular or saw-toothed sweep signal for horizontally sweeping the electron beam at a trace-retrace rate of 60 cycles per second. The 60 $\overline{Hz}$ timing signal (BLNK) is extended to the blanking input (BLNK) of blanking and intensity control circuit 22 to blank the electron beam during the retrace phase of each horizontal sweep cycle.

Referring now to the digitalization of the ECG signal on line 25 and its subsequent storage in memory 27, an analog-to-digital converter is comprised of a ramp control flip-flop 31, a ramp signal generator 32, a comparator 33 and a NOR gate 34. The ramp generator 32 produces a linearly increasing ramp signal that is reset at 8.3-millisecond intervals by the action of the 120 $\overline{Hz}$ clock signal extended to the input of ramp control flip-flop 31 from the output of memory load control circuit 35. The flip-flop 31 holds the ramp reset for about 16 mircoseconds, the half period of the 30 kHz signal that is extended to the reset input of flip-flop 31. The ramp signal from generator 32 is extended to one input of comparator 33, the other input thereto being provided by the ECG signal appearing on line 25.

The output of comparator 33 remains in a "zero" or low state so long as the instant analog amplitude of the ECG signal is greater than the instant amplitude of the ramp, and goes to a "one" or high state when the ramp amplitude exceeds that of the ECG signal. In this manner, the output of comparator 33, extended to an input of NOR gate 34, serves to control the extension of 30 kHz clock pulses appearing at the other input of the NOR gate to the input of a 7 bit binary counter 36. It will be appreciated that the 30 kHz clocking pulses are extended to the input of binary counter 36 only so long as the instant amplitude to the ECG signal exceeds the ramp signal and the output of comparator 33 remains in the "zero" state. In this way, the number of 30 kHz clock pulses registered by binary counter 36 is directly representative digitally of the magnitude of the instant sample of the incoming ECG signal. The seven parallel outputs of binary counter 36 are extended in parallel, as represented by line 37, to seven respective parallel inputs of multiplexer 26. The binary counter 36 is reset to zero by the RESET signal extended thereto from the output of memory load control circuit 35 just before the ramp signal begins its rise during each sample interval.

The memory load control circuit 35 comprises logic having as inputs, the 120 Hz and the 60 kHz timing signals respectively for providing as outputs the RESET signal, a memory LOAD signal, a memory $\overline{\text{LOAD}}$ signal and the $\overline{120}$ Hz signal. The RESET signal occurs at the beginning of each 120 Hz sampling interval and lasts for less than 16 microseconds. The LOAD signal is extended to multiplexer 26 to enable the set of inputs receiving the newly sampled data for entry in memory 27. Accordingly the LOAD signal appears immediately following the termination of a 120 Hz sampling interval and the subsequent RESET signal and is of a duration sufficient only to enter one new data word into shift register memory 27, as determined by the 30 kHz data shift rate. Correspondingly, the $\overline{\text{LOAD}}$ signal enables the complimentary inputs of multiplexer 26 for the remainder of each recirculation cycle.

The SYNC MARKER signal is extended, as represented by line 24, to the remaining input of multiplexer 26 associated with the seven inputs from binary counter 36 and represented by line 37. The SYNC MARKER signal is in the "high" voltage state for an interval which is preselected to exceed the 8.3 millisecond sampling interval to insure that the "high" voltage level appears at the input of multiplexer 26 while a LOAD signal may have a 10 millisecond interval and may in fact result in the entry of two successive marker words in memory 27.

The shifting of data in memory 27 is accomplished by shift pulses extended thereto via lines 38 from pulse drivers 39 which in turn receive drive pulse inputs via lines 40 from EXCLUSIVE OR gate 41 comprising part of a memory shift control circuit 42. 30 kHz timing pulses are provided as one input to EXCLUSIVE OR gate 21 and comprise the basic shift pulses extended to memory 27. Because the display on CRT 19 is to precess (i.e. to move slowly from right to left across the screen), the data in the memory must precess at the same rate relative to the basic system timing. This precession is accomplished by actually over-shifting by one word location in each sampling cycle and is accomplished by the control flip-flop 43 associated with memory shift control 42. The $\overline{\text{LOAD}}$ signal is extended to the clock input of flip-flop 43 in turn having its output extended to the other input of EXCLUSIVE OR gate 41. Under the control of flip-flop 43, the EXCLUSIVE OR gate 41 produces shift pulses on either the high or low state of the 30 kHz signal. Since each change of state of the $\overline{\text{LOAD}}$ signal (and therefore flip-flop 43) coincides with the 60 kHz timing input to memory load control circuit 35, the change of state of flip-flop 43 is itself responsible for the extra shift pulse each cycle.

The memory 27 may be viewed as comprising eight parallel data tracks along which data is shifted in synchronism, seven of the data tracks containing digital data indicative of the amplitude of respective samples of the ECG input signal and the remaining track containing digital data indicative of the existence or nonexistence of a SYNC MARKER signal. At a heart rate of 60 – 70 beats per minute and the 30 kHz shift rate employed herein, the full serial contents of memory 27 typically represent about 4 – 4½ seconds of the real-time ECG signal. Accordingly, one would expect the event marker data track to include about 4 spaced indications of the SYNC MARKER, each said indication comprising one or possibly more serially adjacent binary "1"s. To effect recirculation of the data in memory 27, the seven parallel binary outputs of the other eight bit input of multiplexer 26 via line 44 and the corresponding one bit output of the event data track is extended to the remaining one input of multiplexer 26 via line 45.

Thus, data representative of the most recent 4 – 4½ seconds of the ECG signal and of the existence of a corresponding SYNC MARKER signal are always present in memory 27 with newly sampled data being entered at the appropriate time in each recirculation cycle. The seven parallel output of memory 27 containing ECG data, as represented by line 44, are additionally extended to seven respective inputs of a seven-input, digital-to-analog convertor 46 which returns the digital data representative of the ECG signal to its analog form, as represented by line 47. The D to A conversion circuitry 46 is of any suitable type which includes circuitry for sampling and holding successive outputs of the converter following the first half of the respective converter output period to allow settling of the converted value. Sample signals are provided by the 60 kHz timing signal extended to the sample and hold circuitry of converter 46. The ECG analog signal appearing on line 47 comprises the vertical deflection (VERT DEFL) control signal and accordingly, is extended to the vertical deflection input VERT of display unit 18.

The output of that track of shift register memory 27 containing the SYNC MARKER data, as represented by line 45, is also extended through inverter 49 to an input of NOR gate 48 for selective extension therethrough as the intensity control signal INT which is extended to the intensification input INT of the blanking and intensity control circuit 22. In accordance with the invention, the 3.75 Hz flasher signal is extended to another input of NOR gate 48 to control extension of the SYNC MARKER data to the input INT, and thereby secondarily modulates the intensity control. The remaining input to NOR gate 48 is provided by the 60 $\overline{\text{Hz}}$ blanking signal. The 60 $\overline{\text{Hz}}$ signal holds the output of NOR gate 48 in the low, or disabling, state during retrace to prevent possible short circuiting of the blanking and intensity control circuitry 22 as will become hereinafter evident.

The data appearing on line 45 from the output of the SYNC MARKER data track will be in a logical "1" state if a SYNC MARKER existed in that time increment and is, following inversion by inverter 49, applied as a logical "0" to the input of NOR gate 48. Accordingly, during the trace phase of the horizontal sweep cycle and while the 3.75 Hz flasher signal is in its low state, the output of NOR gate 48 will go to its high state, or a logic "1", each time a "0" representative of a SYNC MARKER event appears at its input. Thus, the output of NOR gate 48 is in the high state only during the trace phase of the sweep and then only when SYNC MARKER data is detected and even further, only during alternate half cycles of the 3.75 Hz waveform. Thus, during the trace phase, the SYNC MARKER acts primarily to increase the intensity of the trace during its existence and secondarily, in conjunction with the 3.75 flasher signal, to periodically modulate the primary control by negating the intensity increase.

The blanking and intensification control circuitry 22 controls the voltage applied to the control grid of the CRT 19. A potentiometer 50 is connected across relatively positive and negative sources of voltage and a resulting control voltage is extended to the control grid of CRT 19 from the wiper of potentiometer 50 and through current limiting resistor 51. The wiper of potentiometer 50 is normally set for a normal or moderate beam intensity level, however this voltage may be alternately increased or decreased to approximately the positive or negative source voltages respectively by turning on a respective one of the normally non-conducting switching transistors 52 or 53. The emitter of switching transistor 52 is connected to the positive voltage source and its collector is connected to the conductor providing the control grid voltage intermediate resistor 51 and the CRT control grid. Switching transistor 53 has its emitter connected to the negative voltage source and its collector connected in common with the collector of transistor 52.

A signal-inverting switching transistor 54 has its emitter connected to the negative voltage source and has its collector connected in the base circuit of transistor 52. A pair of biasing resistors 55 are connected in the base circuit of transistor 54 to normally bias it in the off condition. The intensification signal INT is applied through one of the resistors 55 to the base of transistor 54 and turns the transistor on when it goes to the high state indicative of a SYNC MARKER event.

Switching transistors 52 and 53 are also biased in the normally-off condition by biasing resistor pairs 56 and 57 respectively. When transistor 54 is turned on by a SYNC MARKER event, transistor 52 is similarly turned on, thereby increasing the positive control grid voltage and accordingly the intensity of the beam trace. The 60 $\overline{\text{Hz}}$ blanking signal (BLNK) is extended through one of the biasing resistors 57 to the base of transistor 53 for switching the transistor on during the high, or retrace, phase of the 60 $\overline{\text{Hz}}$ signal. When transistor 53 is turned on, the voltage applied to the CRT's control grid approaches the negative voltage source and is sufficient to blank or suppress the electron beam.

It will be noted that the 60 $\overline{\text{Hz}}$ signal into NOR gate 48 acts to prevent the generation of an intensification signal during the retrace phase of the sweep cycle thereby insuring that transistors 52 and 53 will not be turned on concurrently and result in a short circuit between the positive and negative voltage sources.

The 3.75 Hz flasher signal applied to NOR gate 48, in accordance with the invention, serves during several successive trace sweeps to allow passage of the SYNC MARKER signal through gate 48 to the input INT for locally intensifying section 21 of the displayed waveform 20 (in FIG. 4), and alternately serves during the next several successive trace sweeps to lock the output of gate 48 to "0" such that the local section 21$_a$ of the waveform is of the same intensity as the remainder of the waveform. In this way, the SYNC MARKER 21 appearing in waveform 20 is seen to flash or blink between an intensified and a normal intensity level at a 3.75 Hz rate in order to further emphasize the presence and position of the marker.

Figure 3:
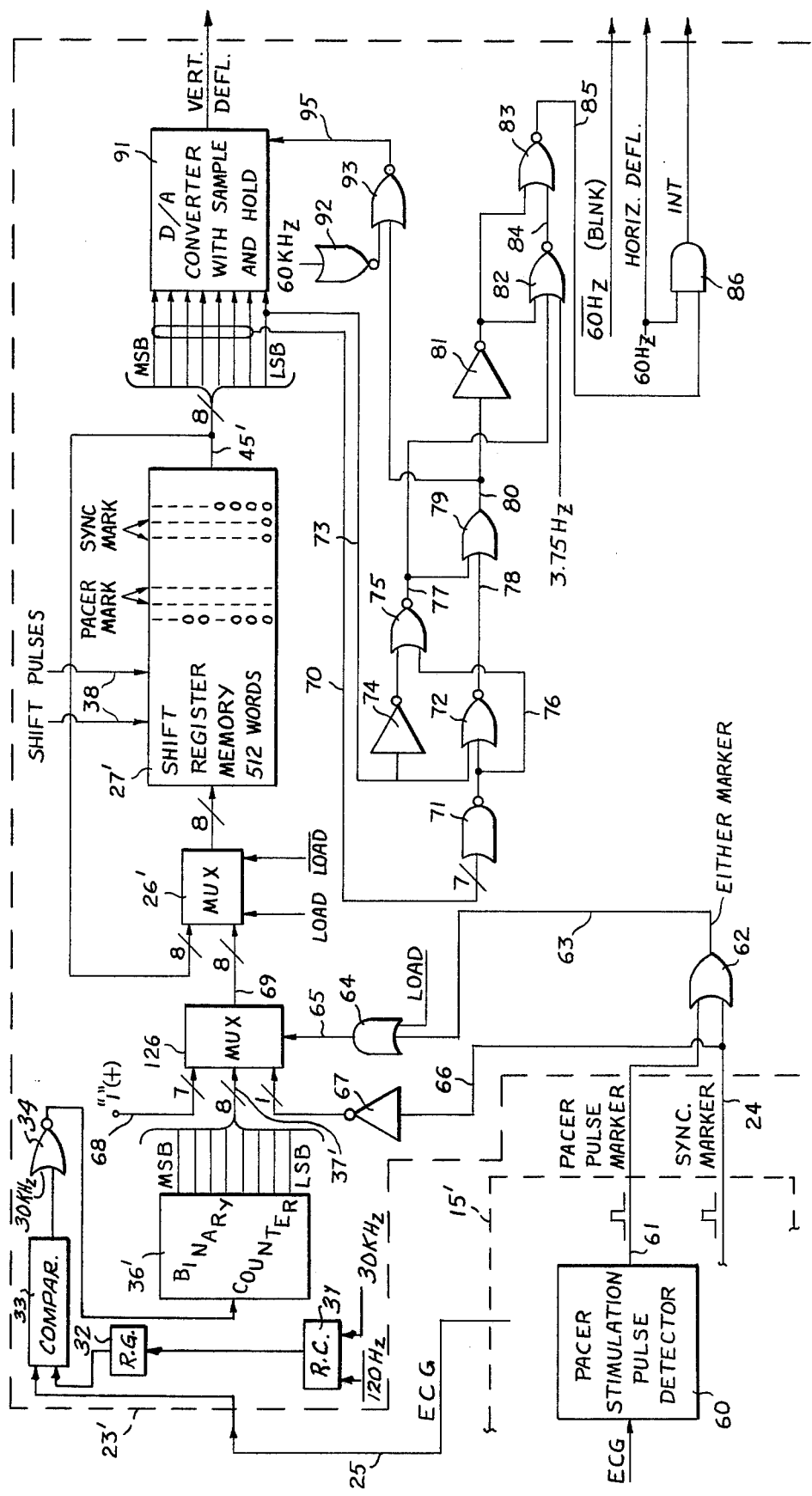
FIG. 3 is a block diagram of an alternate embodiment of the display system illustrated in FIG. 2 in which distinctly different markers are provided for different types of events.

Reference is made now to an alternate embodiment of the display system comprising the invention. Those portions of the embodiment illustrated in FIG. 3 which are identical to those appearing in FIGS. 1 and 2 have either been omitted or identically numbered and the elements performing a generally similar but not identical function have been designated with primed numbers corresponding with their counterparts in FIG. 1 and 2.

In addition to the R-wave detection circuitry associated with ECG amplifying circuitry 15', there is also a pacer stimulation pulse detector 60 of suitable known design which is responsive to the sensed ECG signal to provide an output PACER PULSE MARKER signal, as represented on line 61 and similarly numbered in FIG. 7, if and when a heart pacer stimulation pulse appears in the ECG signal. This will occur if a heart pacer (not shown) is operatively associated with the heart of patient 11 and further has generated a stimulation pulse applied to the heart. It may be desirable for the person monitoring the display to be able to identify not only the occurrence and timing of the defibrillator SYNC pulse but also the occurrence and timing of a stimulation pulse from a heart pacer. The PACER PULSE MARKER signal observes the same constraints as the SYNC MARKER signal as regards its having a minimul interval at least as great as the sampling interval of the display memory and control circuitry 23'. In the illustrated embodiment, the PACER PULSE MARKER signal has the same duration as the SYNC MARKER signal.

As in the embodiment of FIG. 2, the analog ECG signal is digitized with the output of NOR gate 34 being extended to the input of an 8 bit binary counter 36'. The number of stages in 8 bit counter 36' and the high-frequency clock input to NOR gate 34 have been selected such that the seven most significant bits (MFB) of the count accumulated in counter 36' may never all be "1"s. The foregoing limitation is required for the coding of data words entered into memory and permits a distinction to be made between ECG data words and event marker data words, as will hereinafter become evident. The outputs of the eight stages of counter 36' are extended in parallel, as represented by line 37', to a respective set of eight inputs on eight-input multiplexer 126.

The lines on which the PACER PULSE MARKER signal and the SYNC MARKER signal respectively appear are extended to two respective inputs of OR gate 62 in the display memory and control circuitry 23'. The output of OR gate 62, as represented by line 63, is high whenever either marker signal exists to provide a high level at the respective input to the OR gate. This indication of a marker signal is extended, via line 63, to an input of AND gate 64 having the LOAD signal applied as the other input thereto. The output of AND gate 64 is extended via line 65 to the control input of multiplexer 126. The SYNC MARKER signal is extended via line 66 and through inverter 67 to that one of the other eight inputs to multiplexer 126 which is the counterpart of the least significant bit (LSB) input used by the counter 36'. The remaining seven inputs to multiplexer 126 are connected, as represented by line 68, to a voltage source corresponding with a logic "1" signal level.

Thus it will be seen that the inputs to multiplexer 126 corresponding with the marker event data always comprise the seven most significant bits being all "1"s. The least significant bit is a logic "0" only when a SYNC MARKER signal exists. The multiplexer control signal appearing on line 65 will normally be low when neither marker exists and thereby acts to pass the digital data from counter 36' through the multiplexer 126 to its eight outputs indicated by the line 69. However, when either marker is present and a LOAD signal occurs, line 65 goes high and the data representative of a marker event passes through multiplexer 126 to output lines 69. It will be recognized that if the marker event occurring is a SYNC MARKER, the data appearing on line 69 will comprise seven "1"s as the MSB's and a "0" as the LSB and conversely, if a PACER PULSE MARKER is present, the data will be comprised of eight "1"s.

The data from multiplexer 126 is extended, via line 69, to one set of eight inputs on eight-input multiplexer 26' and provides the source of the new data available for entry to the 512 word shift register memory 27' which, as in the embodiment of FIG. 2, is connected for precessive recirculation of the data entered therein. Accordingly, that data which has been shifted through memory 27' and is available for recirculation appears on the eight parallel lines, represented by line 45' extending between the eight parallel outputs of memory 27' and the respective other eight inputs of multiplexer 26'. As previously, the LOAD signal extended to multiplexer 26' effects the entry of new data into memory 27' and the $\overline{\text{LOAD}}$ signal applied to the multiplexer provides for the recirculation of data previously stored in memory. Shift pulses 38 extended to memory 27' control the serial shifting of data therethrough.

It will be appreciated that although shift register memory 27' may be physically identical to memory 27 in FIG. 2, the organization of data therein differs inasmuch as now each of the memory's serially-successive eight-bit word positions identifies only a marker-event, or a magnitude sample of the ECG signal, each marker-event word further identifying the type of event PACER PULSE vs SYNC MARKER as determined by the logic state of the least significant bit. This arrangement of memory 27' results in the event marker words taking precedence over the ECG samples which would otherwise have occupied the particular word positions, however the number of event marker words compared with the total number of ECG data words is sufficiently small that no significant loss of ECG information results. Further, this arrangement permits a data-coding capable of identifying more than one different type of event marker. An event-marker data word is recognized by logic which analyzes the coding of each respective word. The seven most significant bit outputs from memory 27' are extended via line 70 to seven respective inputs of NAND gate 71. The output of NAND gate 71 is extended via line 76 to inputs of NOR gate 72 and 75 respectively. The least significant bit appearing in the output of memory 27' is extended via line 73 to the other input of NOR gate 72 and also through inverter 74 to an input of NOR gate 75.

The output of NAND gate 71 will normally be at the "1" level and will go to the "0" level only when event-marker data appears, as represented by seven "1"s at the inputs of NAND gate 71. Thus the output of NOR gate 75, as represented by line 77, remains a "0" when no marker-event data is present and will go to the "1" state only when STIMULATION PULSE MARKER data appears on line 45' such that the least significant bit represented by line 73 is a "1". Similarly, the output of NOR gate 72, as represented by line 78 extended to the input of OR gate 79, is a "0" whenever ECG data appears on line 45' and goes to a "1" only when SYNC MARKER data is present and the least significant bit appearing on line 73 is a "0". Output 77 from NOR gate 75 also comprises an input to OR gate 79, the output of which as represented by line 80 will be a "1" only when either of the event markers is present.

The signal appearing on line 80 is extended through inverter 81 to inputs of NOR gates 82 and 83 respectively. The signal appearing on line 77 is extended to another input of NOR gate 82 and the final input thereto is provided by the 3.75 Hz flasher signal. The output of NOR gate 82, as represented by line 84, is extended to the other input of NOR gate 83 and will normally be a "0" and may be a "1" only during the appearance of a SYNC MARKER at the output of memory 27' and then only if the 3.75 Hz flasher signal is in its "0" half cycle. The other input to NOR gate 83 will be a "0" only if either of the event markers is present. Therefore, the output of NOR gate 83, represented by line 85, is normally "0" and will be a "1" only whenever a PACER PULSE MARKER is detected from memory or further, only if a SYNC MARKER is detected from memory and then only during alternate half-cycles of the 3.75 Hz flasher signal. This output from NOR gate 83 is extended through AND gate 86 to provide the intensification control signal INT only during the trace phase of the horizontal sweep cycle, as determined by the 60 Hz timing and control signal applied to the other input of the AND gate.

The INT control signal is extended to the input INT of circuitry 22 and causes a section of waveform 20' of FIG. 6 to be intensified, as at 21', for each detection of a SYNC MARKER (shown as 24 in the timing waveform of FIG. 7) in several successive trace sweeps and alternately, during the next several successive trace sweeps, to be of normal intensity, as at $21'_a$, such that section 21' flashes in accordance with the invention as applied in the embodiment of FIG. 2. However, because the output from NOR gate 83 is a "1" each time a PACER PULSE MARKER occurs, the waveform 20' will be intensified at section 90 thereon during each successive sweep. In this way, the observer is readily able to distinguish between the SYNC MARKER and the PACER STIMULATION PULSE on the display, as well as having the basic enhancement of the SYNC MARKER display provided by its flashing as described earlier.

The vertical deflection control signal (VERT DEFL) to display unit 18 is provided by a suitable eight-input digital to analog converter 9, including sample and hold circuitry for sampling the output of the converter following successive conversions. As with D-to-A converter 46 in FIG. 2, a 60 kHz clock signal determines the sampling rate for the D-to-A converter 91. However, because one or more successive ECG data words have been replaced by event-marker data words, it may be desirable that the event marker word not be converted to a component of the vertical deflection control signal. Accordingly, the 60 kHz signal is extended through an inverter 92 to one input of a NOR gate 93, the other input to the NOR gate being provided by line 80 representing the output of OR gate 79. In this way, the 60 kHz sampling clock is applied to D-to-A converter 91, via line 95 from the output of NOR gate 95, only when ECG data words are present and is inhibited by the output of OR gate 79 when either of the event markers is present. Thus, even though one or more successive event marker words may be converted by D-to-A converter 91, the absence of sampling pulses will prevent their entry into the sample and hold circuitry which continues to store the analog value of the last recognized ECG data word.

It will be appreciated that more than two different types of events may be distinctly coded and stored in memory by identifying as a marker event, any word in which the six (6) most significant bits are all "1"s and similarly limiting the content of the ECG samples. Four different events may then be seperately identified.

Further, although the secondary modulation of the displayed trace of the event marker comprised a modulation (flashing) of the beam-intensification signal in the illustrated embodiment, it will be appreciated that other means may be used to effect such secondary modulation. For instance, if the "widening" of the displayed marker is not objectionable, circuitry may be used to provide a first intensification signal of first duration (e.g. 2 bits) and a second such intensification signal of second, visably different duration (e.g. 4 - 6 bits). This alternate operation might be effected following output of the data from memory and would thus need not distort the ECG waveform. Or, where different types of events are to be differently marked, a respective marker length (duration) may be assigned to each different event type. Still further, the secondary modulation might be provided by deflecting the waveform vertically during intensification, as for instance in the FIG. 3 embodiment by passing every 60 kHz sampling signal to the sample and hold circuitry of D-to-A converter 91 such that even the marker-coded (many "1"s) words are also applied as the VERT DEFL control signal.

The foregoing detailed description has been presented for purposes of explanation only and no unnecessary limitation should be understood therefrom, it being understood that various changes may be made in the manner of carrying out the invention, all within the spirit of the guiding principles and teachings provided herein.

What is claimed is:

1. In a system for displaying a physiological waveform, means for generating an electrical signal representative of a particular physiological waveform; means for generating an electrical signal indicative of the occurrence of a preselected event in timed relation to said physiological waveform signal; a cathode ray tube; and display control means responsive to said physiological waveform signal and to said event signal for controlling the display by said cathode ray tube, said display control means including means for providing time-successive samples of said physiological waveform signal, a recirculating memory for the storage of a successive plurality of waveform samples, means for entering data representative of said event signal in said memory in the same said time relation with said waveform samples as said event bears to said physiological waveform signal, means responsive to said successive waveform samples in memory for controlling the deflection of the beam of said cathode ray tube in at least one coordinate direction to provide a trace representative of said waveform and means responsive to said stored event date for variably controlling the intensity of the beam of said cathode ray tube as a primary modulation of the waveform trace to provide a visibly distinguishable event marker and for secondarily modulating said primary modulation of said waveform trace to further enhance display of the event marker.

2. The systems of claim 1 wherein said secondary modulation of said primarily modulated waveform trace comprises periodically also changing the intensity of said intensified beam of said cathode ray tube at a rate to provide visible flashing of the displayed event marker.

3. The system of claim 2 wherein the intensity of the beam of said cathode-ray tube is increased as said first modulation of the waveform trace.

4. The system of claim 3 wherein said periodic change in beam intensity which comprises said second modulation comprises alternately negating and permitting said increase in intensity comprising said first modulation.

5. The system of claim 4 including means providing a periodic blocking signal and wherein said means for primarily and secondarily modulating the intensity of the beam of said cathode ray tube includes means responsive to said stored event data for intensifying the beam of said cathode ray tube, and gating means responsive to said stored event data and to said periodic blocking signal for periodically blocking extension of the stored event data to said beam intensifying means.

6. The system of claim 1 wherein said event data is stored in memory distinct from said waveform sample data stored therein, and wherein said means for primarily and secondarily modulating said waveform trace and said deflecting means respectively include detecting means responsive to said distinctly stored event data and detecting means responsive to said distinctly stored waveform sample data for detecting said event data and said waveform data separately from memory.

7. The system of claim 6 including means providing a periodic blanking signal and wherein said means for variably controlling the intensity of the beam of said cathode ray tube is normally responsive while said detected waveform sample data is displayed to provide a beam of first normal intensity, is responsive to said blanking signal for blanking the beam during retrace, and is responsive to said recovered event data for increasing the beam intensity to a second intensity greater than said first normal intensity as at least said primarily modulation of the waveform trace thereby to visibly contrast the occurrence of said event with the remainder of the waveform displayed by said cathode ray tube.

8. The system of claim 7 wherein said electrical signal representative of said physiological waveform is connected as an input to said event signal generating means and said event signal generating means is responsive to a particular characteristic of said physiological waveform signal for generating said event signal.

9. The system of claim 8 further including synchronized defibrillating means and wherein said particular physiological waveform comprises a patient's electrocardiographic signal, said defibrillating means including synchronizing means responsive to a particular characteristic of said electrocardiographic signal for providing a signal for synchronizing the discharge of defibrillation energy to the patient, said synchronizing signal comprising said preselected event signal.

10. The system of claim 6 additionally including means for providing a periodic blocking signal and wherein said means for primarily and secondarily modulating the waveform trace further include gating means responsive to said detected event data and to said periodic blocking signal for periodically blocking extension of said detected event data to said beam intensifying means thereby to provide said second modulation, the rate of said periodic blocking signal being preselected to provide visible flashing of the displayed event marker.

11. The system of claim 6 wherein said memory comprises plural parallel data tracks, said waveform sample data being stored and recirculated in less than all of said parallel data tracks and said event data being stored and recirculated in at least one of the remaining said parallel data tracks, the data stored in all of said parallel data tracks being recirculated in synchrony.

12. The system of claim 11 wherein said waveform sample data and said event data are stored and serially recirculated entirely in different ones of said plural parallel data tracks.

13. The system of claim 12 wherein said memory is digital, said data stored in memory is in digital form, said means for detecting said waveform sample data in said memory comprises digital to analog converting means operatively connected to said waveform data track for successive conversion of said digital waveform data to analog form, and said means for detecting said event data in said memory comprises means operatively connected to said event data track in time-parallel relationship with said waveform data detecting means.

14. The system of claim 6 wherein said event-signal generating means is responsive to a first preselected event to generate a respective first event signal and is responsive to a second preselected event different than said first event to generate a second event signal, said first and said second events each having a respective timed relationship with said physiological waveform.

15. The system of claim 14 wherein said memory is digital, said display control means further includes means responsive to said first and said second event signals for digitally coding and entering respective first and second event data in said memory at respective first and second time-locations relative to said waveform sample data, said first event data being coded differently than said second event data, said event data detecting means being responsive to each of said different first and second event data codes for detecting and providing respectively distinct first and second detected event data signals therefor, and said means for primarily and secondarily modulating said waveform trace includes means responsive to said first and said second detected event data signals for increasing the intensity of the beam of said cathode-ray tube for the respective detected event data signals as said primary modulation of the waveform trace and means responsive only to a preselected particular one of said detected first and second event data signals to secondarily modulate the waveform trace for only said one of the first and second event data signals, thereby to distinguish the respective first and second event markers on the waveform trace.

16. The system of claim 15 wherein said means for primarily and secondarily modulating the waveform trace include gating means responsive to said only one of said detected first and second event data signals and to a periodic blocking signal for periodically blocking extension of said only one of said detected first and second event data signals to said beam intensifying means thereby to provide said secondary modulation therefor, the rate of said periodic blocking signal being preselected to provide visible flashing of the respective displayed event marker.

17. The system of claim 16 wherein said memory comprises a successive plurality of multibit, digital word positions, said waveform samples being digitally coded and respectively entered as successive words in said memory, said first and said second coded event data being entered as respective words in said memory and superseding said waveform sample words coincidental therewith, said waveform sample words being coded differently than either of said first and said second event data words and said event data detecting means being responsive only to the coding of said first and said second event data words.

18. The system of claim 17 wherein said waveform sample detecting means comprises digital to analog conversion means including sample and hold circuit means, sampling signal means extended to said sample and hold means for sampling analog levels of successive digital words in said memory, means for providing an inhibit signal in response to said detection of either of said first or second event data signals, and means responsive to said inhibit signal for inhibiting said sampling signal from said sample and holds circuit means when either of said first or said second event data signals is detected, thereby to extend the hold of the last data-word sampled by said sample and hold circuit while either of said detected first or second event data signals exists.

19. The system of claim 18 further including synchronized defibrillating means and means for detecting the stimulation pulse of a heart pacer operatively associated with a patient's heart, said particular physiological waveform comprising the patient's electrocardiographic signal, said defibrillating means including synchronizing means responsive to a particular characteristic of said electrocardiographic signal for providing a signal for synchronizing the discharge of defibrillating energy to a patient, said synchronizing signal comprising one of said first and said second preselected event signals, said stimulation pulse detecting means being responsive to a particular characteristic of said electrocardiographic signal for providing a signal indicative of a pacer stimulation pulse, said pacer pulse indicating signal comprising the other of said first and said second preselected event signals.

* * * * *